(12) United States Patent
Johnston et al.

(10) Patent No.: US 7,820,852 B2
(45) Date of Patent: Oct. 26, 2010

(54) DIRECT AND SELECTIVE PRODUCTION OF ETHYL ACETATE FROM ACETIC ACID UTILIZING A BIMETAL SUPPORTED CATALYST

(75) Inventors: Victor J. Johnston, Houston, TX (US); James H. Zink, League City, TX (US); Deborah R. Repman, Lake Jackson, TX (US); Laiyuan Chen, Houston, TX (US); Barbara F. Kimmich, League City, TX (US); Josefina T. Chapman, Houston, TX (US); Jan Cornelis van der Waal, Delft (NL); Virginie Zuzaniuk, Krommenie (NL)

(73) Assignee: Celanese International Corporation, Dallas, TX (US)

( * ) Notice: Subject to any disclaimer, the term of this patent is extended or adjusted under 35 U.S.C. 154(b) by 0 days.

(21) Appl. No.: 12/221,209

(22) Filed: Jul. 31, 2008

(65) Prior Publication Data
US 2010/0029980 A1 Feb. 4, 2010

(51) Int. Cl.
*C07C 69/02* (2006.01)
(52) U.S. Cl. .................................................. 560/231
(58) Field of Classification Search ............... None
See application file for complete search history.

(56) References Cited

U.S. PATENT DOCUMENTS

| | | |
|---|---|---|
| 2,607,807 A | 8/1952 | Ford ........................ 270/638 |
| 2,882,244 A | 4/1959 | Milton ...................... 252/455 |
| 3,130,007 A | 4/1964 | Breck ........................ 23/113 |
| 3,702,886 A | 11/1972 | Argauer et al. ............. 423/328 |
| 4,275,228 A | 6/1981 | Gruffaz et al. |
| 4,337,351 A | 6/1982 | Larkins, Jr. |
| 4,374,265 A | 2/1983 | Larkins, Jr. |
| 4,398,039 A | 8/1983 | Pesa et al. |
| 4,443,639 A | 4/1984 | Pesa et al. |
| 4,465,854 A | 8/1984 | Pond et al. |
| 4,471,136 A | 9/1984 | Larkins et al. |
| 4,480,115 A | 10/1984 | McGinnis |
| 4,517,391 A | 5/1985 | Schuster et al. ............ 568/885 |
| 4,777,303 A | 10/1988 | Kitson et al. |
| 4,804,791 A | 2/1989 | Kitson et al. |
| 4,826,795 A | 5/1989 | Kitson et al. |
| 4,886,905 A | 12/1989 | Larkins, Jr. |
| 4,985,572 A | 1/1991 | Kitson et al. |
| 5,137,861 A | 8/1992 | Shih et al. |
| 5,149,680 A * | 9/1992 | Kitson et al. ............... 502/185 |
| 5,155,084 A | 10/1992 | Horn et al. |
| 5,241,106 A | 8/1993 | Inoue et al. |
| 5,243,095 A | 9/1993 | Roberts et al. |
| 5,350,504 A | 9/1994 | Dessau |
| 5,475,144 A | 12/1995 | Watson et al. |
| RE35,377 E | 11/1996 | Steinberg et al. ........... 518/704 |
| 5,821,111 A | 10/1998 | Grady et al. ............ 435/252.5 |
| 5,861,530 A | 1/1999 | Atkins et al. |
| 5,973,193 A | 10/1999 | Crane et al. |
| 6,232,352 B1 | 5/2001 | Vidalin ...................... 518/700 |
| 6,462,231 B1 | 10/2002 | Yanagawa et al. |
| 6,495,730 B1 | 12/2002 | Konishi et al. |
| 6,632,330 B1 | 10/2003 | Colley et al. |
| 6,657,078 B2 | 12/2003 | Scates et al. ................ 562/519 |
| 6,685,754 B2 | 2/2004 | Kindig et al. ................. 48/210 |
| 6,693,213 B1 | 2/2004 | Kolena et al. |
| 6,765,110 B2 | 7/2004 | Warner et al. |
| 6,768,021 B2 | 7/2004 | Horan et al. |
| 6,906,228 B2 | 6/2005 | Fischer et al. |
| 7,425,657 B1 | 9/2008 | Elliott et al. |
| 7,538,060 B2 | 5/2009 | Barnicki et al. |
| 7,553,397 B1 | 6/2009 | Colley et al. |
| 2003/0013908 A1 | 1/2003 | Horan et al. |
| 2006/0019360 A1 | 1/2006 | Verser et al. |
| 2008/0207953 A1 | 8/2008 | Houssin et al. |
| 2009/0005588 A1 | 1/2009 | Hassan et al. |
| 2009/0221725 A1 | 9/2009 | Chornet et al. |
| 2009/0326080 A1 | 12/2009 | Chornet et al. |
| 2010/0016454 A1 | 1/2010 | Gracey et al. |
| 2010/0029995 A1 | 2/2010 | Johnson et al. |
| 2010/0121114 A1 | 5/2010 | Weiner et al. |

FOREIGN PATENT DOCUMENTS

| | | |
|---|---|---|
| EP | 0198682 | 10/1986 |
| EP | 0285420 | 5/1988 |
| EP | 0372847 | 6/1990 |
| EP | 400904 | * 12/1990 |
| GB | 1168785 | 10/1969 |
| GB | 1559540 | 1/1980 |

(Continued)

OTHER PUBLICATIONS

U.S. Appl. No. 12/319,121, filed Dec. 31, 2008, Johnston et al.

(Continued)

*Primary Examiner*—Karl J Puttlitz

(57) ABSTRACT

A process for the selective production of ethyl acetate by vapor phase reaction of acetic acid over a hydrogenating catalyst composition to form ethyl acetate is disclosed and claimed. In an embodiment of this invention reaction of acetic acid and hydrogen over platinum and copper supported on silica selectively produces ethyl acetate in a vapor phase at a temperature of about 250° C.

52 Claims, No Drawings

FOREIGN PATENT DOCUMENTS

| | | |
|---|---|---|
| GB | 2 136 704 A | 9/1987 |
| JP | 10-306047 A | 11/1998 |
| JP | 2001-046874 A | 2/2001 |
| JP | 2001-157841 A | 6/2001 |

OTHER PUBLICATIONS

Brunauer Emmett and Teller J. Am. Chem. Soc. 60,309 (1938); Proc. Roy. Soc. A314, pp. 473-498; and Mol. Sieves Pap. Conf., 1967, 78, Soc. Chem. Ind. London, by D. Domine and J. Quobex.

International Search Report and Written Opinion for PCT/US2009/004197 mailed Mar. 24, 2010 (14 pages).

International Search Report and Written Opinion for PCT/US2009/004195 mailed Mar. 26, 2010 (12 pages).

Pallasana et al., Reaction Paths in the Hydrogenolysis of Acetic Acid to Ethanol over Pd(111), Re(0001), and PdRe Alloys, Journal of Catalysis 209:289-305 (2002).

Pestman et al., Reactions of Carboxylic Acids on Oxides, Journal of Catalysis 168:255-264 (1997).

Pestman et al., Identification of the Active Sites in the Selective Hydrogenation of Acetic Acid to Acetaldehyde on Iron Oxide Catalysts, Journal of Catalysis 174:142-152 (1998).

Zheng, et al. (2007). Preparation and catalytic properties of a bimetallic Sn-Pt complex in the supercages of NaY zeolite by use of surface organometallic chemistry, Applied Organometallic Chemistry, 21(10), 836-840.

Santori et al. (2000). Hydrogenation of carbonylic compounds on Pt/SiO2 catalysts modified with SnBu4, Studies in Surface Science and Catalysis, 130, 2063-2068.

Rachmady, Acetic Acid Reduction by H2 on Bimetallic Pt—Fe Catalysts, Journal of Catalysis 209, 87-98 (Apr. 1, 2002), Elsevier Science (USA).

Ordóñez et al., The role of metal and support sites on the hydrogenation of acetic acid on Ru-based catalysts, 21st NAM San Francisco, CA, Jun. 10, 2009.

Gursahani et al., Reaction kinetics measurements and analysis of reaction pathways for conversions of acetic acid, ethanol, and ethyl acetate over silica-supported Pt, Applied Catalysis A: General 222 (2001) 369-392.

Amit M. Goda et al., DFT modeling of selective reduction of acetic acid to acetaldehyde on Pt-based bimetallic catalysts, 20th NAM, Houston, TX, Jun. 17-22, 2007 available online at < http://www.nacatsoc.org/20nam/abstracts/O-S9-18.pdf>.

Acala, et al.,(2005). Experimental and DFT studies of the conversion of ethanol and acetic acid on PtSn-based catalysts, Journal of Physical Chemistry, 109(6), 2074-2085.

* cited by examiner

DIRECT AND SELECTIVE PRODUCTION OF ETHYL ACETATE FROM ACETIC ACID UTILIZING A BIMETAL SUPPORTED CATALYST

FIELD OF THE INVENTION

The present invention relates generally to a process for the production of ethyl acetate from acetic acid. More specifically, the present invention relates to a process including hydrogenating acetic acid utilizing a catalyst composed of a supported bimetal catalyst, such as for example, platinum or palladium and copper or cobalt supported on a suitable catalyst support optionally containing one or more additional hydrogenating metals to form ethyl acetate with high selectivity.

BACKGROUND

There is a long felt need for an economically viable process to convert acetic acid to ethyl acetate. Ethyl acetate is an important commodity feedstock for a variety of industrial products and is also used as an industrial solvent in the manufacture of various chemicals. For instance, ethyl acetate can readily be converted to ethylene by subjecting it to a cracking process, which can then be converted to a variety of other products. Ethyl acetate is conventionally produced from feedstocks where price fluctuations are becoming more significant. That is, fluctuating natural gas and crude oil prices contribute to fluctuations in the cost of conventionally produced, petroleum or natural gas-sourced ethyl acetate, making the need for alternative sources of ethyl acetate all the greater when oil prices rise.

The hydrogenation of carboxylic acids over heterogeneous catalysts to produce alcohols is well reported. For instance, U.S. Pat. No. 2,607,807 discloses that ethanol can be formed from acetic acid over a ruthenium catalyst at extremely high pressures of 700-950 bar in order to achieve yields of around 88%, whereas low yields of only about 40% are obtained at pressures of about 200 bar. However such extreme reaction conditions are unacceptable and uneconomical for a commercial operation.

More recently, even though it may not still be commercially viable it has been reported that ethanol can be produced from hydrogenating acetic acid using a cobalt catalyst at superatmospheric pressures such as about 40 to 120 bar. See, for example, U.S. Pat. No. 4,517,391 to Shuster et al.

On the other hand, U.S. Pat. No. 5,149,680 to Kitson et al. describes a process for the catalytic hydrogenation of carboxylic acids and their anhydrides to alcohols and/or esters utilizing a platinum group metal alloy catalyst. The catalyst is comprised of an alloy of at least one noble metal of Group VIII of the Periodic Table and at least one metal capable of alloying with the Group VIII noble metal, admixed with a component comprising at least one of the metals rhenium, tungsten or molybdenum. Although it has been claimed therein that improved selectivity to a mixture of alcohol and its ester with the unreacted carboxylic acid is achieved over the prior art references it was still reported that 3 to 9 percent of alkanes, such as methane and ethane are formed as by-products during the hydrogenation of acetic acid to ethanol under their optimal catalyst conditions.

A slightly modified process for the preparation of ethyl acetate by hydrogenating acetic acid has been reported in EP 0 372 847. In this process, a carboxylic acid ester, such as for example, ethyl acetate is produced at a selectivity of greater than 50% while producing the corresponding alcohol at a selectivity less than 10% from a carboxylic acid or anhydride thereof by reacting the acid or anhydride with hydrogen at elevated temperature in the presence of a catalyst composition comprising as a first component at least one of Group VIII noble metal and a second component comprising at least one of molybdenum, tungsten and rhenium and a third component comprising an oxide of a Group IVb element. However, even the optimal conditions reported therein result in significant amounts of by-products including methane, ethane, acetaldehyde and acetone in addition to ethanol. In addition, the conversion of acetic acid is generally low and is in the range of about 5 to 40% except for a few cases in which the conversion reached as high as 80%.

From the foregoing it is apparent that existing processes do not have the requisite selectivity to ethyl acetate or existing art employs catalysts, which are expensive and/or non-selective for the formation of ethyl acetate and produces undesirable by-products.

SUMMARY OF THE INVENTION

Surprisingly, it has now been unexpectedly found that ethyl acetate can be made on an industrial scale directly from acetic acid with very high selectivity and yield. More particularly, this invention provides a process for the selective formation of ethyl acetate from acetic acid comprising: hydrogenating acetic acid in the presence of hydrogen over a hydrogenating catalyst comprising at least one metal selected from the group consisting of nickel, platinum and palladium and at least one metal selected from molybdenum, rhenium, zirconium, copper and cobalt with the proviso that platinum may be used without molybdenum, rhenium, zirconium, copper or cobalt. In addition, the catalyst is comprised of a suitable catalyst support optionally including one or more metal catalysts selected from the group consisting of ruthenium, iridium, chromium, tin, tungsten, vanadium and zinc. More specifically, the catalyst suitable for the process of this invention is typically comprised of a combination of platinum and copper supported on a suitable catalyst support or palladium and cobalt supported on a suitable catalyst support. Suitable catalyst supports include without any limitation, silica, alumina, calcium silicate, carbon, zirconia, zirconia-silica, titania, titania-silica, iron oxide and zeolite catalysts such as for example H-ZSM-5.

In another aspect of this invention a combination of copper/zirconium supported on a suitable catalyst support such as silica is also a suitable catalyst for the selective hydrogenation of acetic acid to ethyl acetate in accordance with the practice of this invention.

DETAILED DESCRIPTION OF THE INVENTION

The invention is described in detail below with reference to numerous embodiments for purposes of exemplification and illustration only. Modifications to particular embodiments within the spirit and scope of the present invention, set forth in the appended claims, will be readily apparent to those of skill in the art.

Unless more specifically defined below, terminology as used herein is given its ordinary meaning. Mole percent (mole % or %) and like terms refer to mole percent unless otherwise indicated. Weight percent (wt % or %) and like terms refer to weight percent unless otherwise indicated.

Typically, the catalyst metal loadings are expressed as weight percent of a catalyst metal based on the total dry weight of the metal and catalyst support. Thus, for example, one (1) weight percent of metal on a support means that one gram of pure metal is present in 100 grams of supported metal catalyst, i.e., the combined weight of support (99 grams) and the metal (1 gram).

"Conversion" is expressed as a mole percentage based on acetic acid in the feed. The conversion of acetic acid (AcOH) is calculated from gas chromatography (GC) data using the following equation:

$$\text{AcOH conversion}(\%) = 100 * \frac{\text{mmol AcOH in(feed stream)} - \text{mmol AcOH out}(GC)}{\text{mmol AcOH in(feed stream)}}$$

"Selectivity" is expressed as a mole percent based on converted acetic acid. For example, if the conversion is 50 mole % and 50 mole % of the converted acetic acid is converted to ethyl acetate (EtOAC), we refer to the ethyl acetate selectivity as 50%. Selectivity is calculated from gas chromatography (GC) data using the following equation:

$$\text{Selectivity to EtOAc}(\%) = 100 * \frac{\text{mmol EtOAc out}(GC)}{\frac{\text{Total mmol C out}(GC)}{2} - \text{mmol AcOH out}(GC)}$$

wherein "Total mmol C out (GC)" refers to total mmols of carbon from all of the products analyzed by gas chromatograph.

The reaction proceeds in accordance with the following chemical equation:

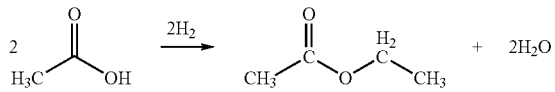

In accordance with the invention, conversion of acetic acid to ethyl acetate can be carried out in a variety of configurations, such as for example in a single reaction zone which may be a layered fixed bed, if so desired. An adiabatic reactor could be used, or a shell and tube reactor provided with a heat transfer medium could be used. The fixed bed can comprise a mixture of different catalyst particles or catalyst particles which include multiple catalysts as further described herein. The fixed bed may also include a layer of particulate material making up a mixing zone for the reactants. A reaction mixture including acetic acid, hydrogen and optionally an inert carrier gas is fed to the bed as a stream under pressure to the mixing zone. The stream is subsequently supplied (by way of pressure drop) to the reaction zone or layer. Reaction zone comprises a catalytic composition including a suitable hydrogenating catalyst where acetic acid is hydrogenated to produce ethyl acetate. Any suitable particle size may be used depending upon the type of reactor, throughput requirements and so forth.

Although various metal supported hydrogenating catalysts known to one skilled in the art can be employed in hydrogenating acetic acid to form ethyl acetate in the process of this invention it is preferred that a hydrogenating catalyst employed is comprised of at least one metal selected from the group consisting of nickel, platinum and palladium and at least one metal selected from molybdenum, rhenium, zirconium, copper and cobalt. In addition, the catalyst is comprised of a suitable catalyst support optionally including one or more metal catalysts selected from the group consisting of ruthenium, iridium, chromium, tin, tungsten, vanadium and zinc. However, single supported metal catalyst such as platinum alone supported on a suitable catalyst support such as titania may also be employed in the process of this invention.

Preferably, the catalyst suitable for the process of this invention is comprised of a combination of platinum and copper supported on a suitable catalyst support or palladium and cobalt supported on a suitable catalyst support. Typically, it is preferred that a suitable weight ratio of a combination of metals on a suitable support can be used as a hydrogenating catalyst. Thus, for example, a combination of platinum and copper (Pt/Cu) or palladium and cobalt (Co) in the weight ratio of about 0.1-1 are particularly preferred. More preferably, a weight ratio of Pt/Cu or Pd/Co is about 0.2-0.5 and most preferably the weight ratio of Pt/Cu or Pd/Co is about 0.2.

The other catalysts suitable in the process of this invention include a bimetallic combination of nickel/molybdenum (Ni/Mo), palladium/molybdenum (Pd/Mo) or platinum/molybdenum (Pt/Mo) supported on H-ZSM-5, silica or carbon. In this aspect of the invention the loading levels of a bimetallic combination of Ni/Mo may be any level to affect the selective hydrogenation of acetic acid to ethyl acetate and typically it is about 1 weight percent nickel and 5 weight percent molybdenum (1 wt % Ni/5 wt % Mo) supported on carbon.

In another aspect, the loading levels of a bimetallic combination of Pd/Mo is about 1 weight percent palladium and 5 weight percent molybdenum (1 wt % Pd/5 wt % Mo) supported on H-ZSM-5 or silica. Similarly, a bimetallic combination of Pt/Mo with a loading of about 1 weight percent platinum and 5 weight percent molybdenum (1 wt % Pt/5 wt % Mo) supported on silica or carbon can also be employed.

In another aspect of this invention, the catalyst is chosen from a bimetallic combination of nickel/rhenium (Ni/Re) or palladium/rhenium supported on titania. Again, in this aspect of the invention any suitable metal loadings can be employed to bring about the selective hydrogenation of acetic acid to ethyl acetate. For instance a bimetallic combination of 1 weight percent nickel and 5 weight percent rhenium (1 wt % Ni/5 wt % Re) supported on titania or a bimetallic combination of 1 weight percent palladium and 5 weight percent rhenium (1 wt % Pd/5 wt % Re) supported on titania can be employed.

In another embodiment of this invention there is also provided a process for selective and direct formation of ethyl acetate from acetic acid comprising: contacting a feed stream containing acetic acid and hydrogen at an elevated temperature with a suitable hydrogenating catalyst containing about 0.5 weight percent to about 1 weight percent of palladium and 2.5 weight percent to about 5 weight percent of rhenium on a suitable catalyst support. More specifically, the catalyst support contains palladium at a loading level of about one (1) weight percent and rhenium at a loading level of about five (5) weight percent and the catalyst support is titania.

In this aspect of the invention, the reactants consist of acetic acid and hydrogen with a molar ratio in the range of about 1:10 to 1:5, the temperature of the reaction zone is in the range of about 225° C. to 275° C., and the pressure of the reaction zone is in the range of about 10 to 20 atmospheres absolute.

Various catalyst supports known in the art can be used to support the catalysts of this invention. Examples of such supports include without any limitation, zeolite, such as H-ZSM-5, iron oxide, silica, alumina, titania, zirconia, magnesium oxide, calcium silicate, carbon, graphite and a mixture thereof. Preferred supports are silica, alumina, calcium silicate, carbon, zirconia and titania. More preferably silica is used as a catalyst support in the process of this invention. It is also important to note that higher the purity of silica, the better it is as a support.

In another aspect of the process of this invention, any of known zeolite catalysts can also be employed as a catalyst support. While any zeolite having a pore diameter of at least about 0.6 nm can be used, preferably employed among such zeolites are the catalyst supports selected from the group consisting of mordenites, ZSM-5, a zeolite X and a zeolite Y.

The preparation of large-pore mordenites is described, for example, in U.S. Pat. No. 4,018,514 and in Mol. Sieves Pap. Conf., 1967, 78, Soc. Chem. Ind. London, by D. DOMINE and J. QUOBEX.

Zeolite X is described, for example, in U.S. Pat. No. 2,882,244 and zeolite Y in U.S. Pat. No. 3,130,007.

Various zeolites and zeolite-type materials are known in the art for the catalysis of chemical reactions. For example, U.S. Pat. No. 3,702,886, of Argauer, discloses a class of synthetic zeolites, characterized as "Zeolite ZSM-5", which are effective for the catalysis of various hydrocarbon conversion processes.

The zeolites suitable for the procedure of the invention can be in the basic form, in the partially or totally acidified form, or in the partially dealuminated form.

Preferably, the zeolite catalyst support in the process of the present invention are in the protic form, characterized as "H-ZSM-5" or "H-mordenite" zeolites, which are prepared from a corresponding "ZSM-5" zeolite or "mordenite" zeolite by replacing most, and generally at least about 80% of the cations of the latter zeolite with hydrogen ions using techniques well-known in the art. These zeolite catalysts are essentially crystalline aluminosilicates or in the neutral form a combination of silica and alumina in a well defined crystalline structure. In a particularly preferred class of zeolite catalysts for purposes of the present invention, the molar ratio of $SiO_2$ to $Al_2O_3$ in these zeolites is within the ratio of about 10 to 60.

In another aspect of this invention, the combination of catalyst metals, palladium and cobalt or a combination of platinum and copper are supported on a high purity low surface area silica or H-ZSM-5 using the procedures well known in the art or the procedures further described herein. Other preferred catalyst supports for platinum or palladium based metal catalysts are carbon, titania and zirconia.

In another embodiment of this invention the preferred catalyst support is carbon. Various forms of carbon known in the art that are suitable as catalyst support can be used in the process of this invention. Particularly preferred carbon support is a graphitized carbon, particularly the high surface area graphitized carbon as described in Great Britain Patent No. 2,136,704. The carbon is preferably in particulate form, for example, as pellets. The size of the carbon particles will depend on the pressure drop acceptable in any given reactor (which gives a minimum pellet size) and reactant diffusion constraint within the pellet (which gives a maximum pellet size).

The carbon catalyst supports that are suitable in the process of this invention are preferably porous carbon catalyst supports. With the preferred particle sizes the carbon will need to be porous to meet the preferred surface area characteristics.

The catalyst supports including the carbon catalyst supports may be characterized by their BET, basal plane, and edge surface areas. The BET surface area is the surface area determined by nitrogen adsorption using the method of Brunauer Emmett and Teller J. Am. Chem. Soc. 60, 309 (1938). The basal plane surface area is the surface area determined from the heat of adsorption on the carbon of n-dotriacontane from n-heptane by the method described in Proc. Roy. Soc. A314 pages 473-498, with particular reference to page 489. The edge surface area is the surface area determined from the heat of adsorption on the carbon of n-butanol from n-heptane as disclosed in the Proc. Roy. Soc. article mentioned above with particular reference to page 495.

The preferred carbon catalyst supports for use in the present invention have a BET surface area of at least 100 $m^2/g$, more preferably at least 200 $m^2/g$, most preferably at least 300 $m^2/g$. The BET surface area is preferably not greater than 1000 $m^2/g$, more preferably not greater than 750 $m^2/g$.

It is possible to use carbon catalyst supports with ratios of basal plane surface area to edge surface area of at least 10:1, preferably at least 100:1. It is not believed that there is an upper limit on the ratio, although in practice it will not usually exceed 200:1.

The preferred carbon support may be prepared by heat treating a carbon-containing starting material. The starting material may be an oleophillic graphite e.g. prepared as disclosed in Great Britain Patent No. 1,168,785 or may be a carbon black.

However, oleophillic graphites contain carbon in the form of very fine particles in flake form and are therefore not very suitable materials for use as catalyst supports. We prefer to avoid their use. Similar considerations apply to carbon blacks which also have a very fine particle size.

The preferred materials are activated carbons derived from vegetable materials e.g. coconut charcoal, or from peat or coal or from carbonizable polymers. The materials subjected to the heat treatment preferably have particle sizes not less than these indicated above as being preferred for the carbon support.

The preferred starting materials have the following characteristics: BET surface area of at least 100 $m^2/g$, more preferably at least 500 $m^2/g$.

One preferred heat treatment procedure for preparing carbon supports having the defined characteristics, comprise successively (1) heating the carbon in an inert atmosphere at a temperature of from 900° C. to 3300° C., (2) oxidizing the carbon at a temperature between 300° C. and 1200° C., (3) heating in an inert atmosphere at a temperature of between 900° C. and 3000° C.

The oxidation step is preferably carried out at temperatures between 300° and 600° C. when oxygen (e.g. as air) is used as the oxidizing agent.

The duration of the heating in inert gas is not critical. The time needed to heat the carbon to the required maximum temperature is sufficient to produce the required changes in the carbon.

The oxidation step must clearly not be carried out under conditions such that the carbon combusts completely. It is preferably carried out using a gaseous oxidizing agent fed at a controlled rate to avoid over oxidation. Examples of gaseous oxidizing agents are steam, carbon dioxide, and gases containing molecular oxygen, e.g. air. The oxidation is preferably carried out to give a carbon weight loss of at least 10 weight percent based on weight of carbon subjected to the oxidation step, more preferably at least 15 weight percent.

The weight loss is preferably not greater than 40 weight percent of the carbon subjected to the oxidation step, more preferably not greater than 25 weight percent of the carbon.

The rate of supply of oxidizing agent is preferably such that the desired weight loss takes place over at least 2 hours, more preferably at least 4 hours.

Where an inert atmosphere is required it may be supplied by nitrogen or an inert gas.

As noted above, the loading levels of a combination of two metal catalysts are generally referenced with the content of main catalyst metal and the weight ratio of the combination. For instance, the weight ratio of Pt/Cu or Pd/Co is in the range of about 0.1 to 2. Thus, when the weight ratio of Pt/Cu or Pd/Co is 0.1, the amount of platinum or palladium can be 0.1 or 1 weight percent and thus 1 or 10 weight percent of copper or cobalt is present on the catalyst support. More preferably, the weight ratio of Pt/Cu or Pd/Co is about 0.5, and thus the amount of platinum or palladium on the catalyst support can be either 0.5 or 1 weight percent and that of copper or cobalt is either one or two weight percent. More preferably, the weight ratio of Pt/Cu or Pd/Co is one or 0.2. Thus the amount of platinum or palladium on a support is 0.5, one or two weight percent and that of copper or cobalt is also 0.5, one or two weight percent when the weight ratio is one. Similarly, when a weight ratio of Pt/Cu or Pd/Co is 0.2, the amount of platinum or palladium on the support can be 0.5 or one weight percent and of copper or cobalt is either 2.5 or five weight percent.

The amount of third metal loading if present on a support is not very critical in this invention and can vary in the range of about 0.1 weight percent to about 10 weight percent. A metal loading of about 1 weight percent to about 6 weight percent based on the weight of the support is particularly preferred.

The metal impregnation can be carried out using any of the known methods in the art. Typically, before impregnation the supports are dried at 120° C. and shaped to particles having size distribution in the range of about 0.2 to 0.4 mm. Optionally the supports may be pressed, crushed and sieved to a desired size distribution. Any of the known methods to shape the support materials into desired size distribution can be employed.

For supports having low surface area, such as, for example, alpha-alumina, the metal solutions are added in excess until complete wetness or excess liquid impregnation so as to obtain desirable metal loadings.

As noted above, the hydrogenation catalysts used in the process of this invention are at least bimetallic containing platinum/copper, palladium/cobalt and so on. Generally, without intending to be bound by any theory, it is believed that one metal acts as a promoter metal and another metal is the main metal. For instance, in the instant process of the invention, of the above noted combinations respectively platinum, palladium, and copper are considered as main metals for preparing hydrogenation catalysts of this invention. The other metals, copper with platinum, cobalt with palladium are considered to be the promoter metals depending upon various reaction parameters including but not limited to catalyst support employed, reaction temperature and pressure, etc. The catalysts may include other promoter metals, such as tungsten, vanadium, molybdenum, chromium or zinc.

The bimetallic catalysts are generally impregnated in two steps. Each impregnation step is followed by drying and calcination. The bimetallic catalysts may also be prepared by co-impregnation. In most cases, the impregnation may be carried out using metal nitrate solutions. However, various other soluble salts which upon calcination release metal ions can also be used. Examples of other suitable metal salts for impregnation include metal oxalate, metal hydroxide, metal oxide, metal acetate, ammonium metal oxide, such as ammonium heptamolybdate hexahydrate, metal acids, such as perrhenic acid solution, and the like.

Thus in one embodiment of this invention, there is provided a hydrogenation catalyst wherein the catalyst support is silica with a bimetallic loading of platinum and copper. In this aspect of the invention, the loading of platinum is about 0.5 weight percent to about 1 weight percent and the loading of copper is about 2.5 weight percent to about 5 weight percent. Specifically, platinum/copper loading levels of 1/1, 1/5, 0.5/0.5, and 0.5/2.5 weight percent on silica can be used.

In another embodiment of this invention, there is further provided a hydrogenation catalyst wherein the catalyst support is high purity low surface area silica with a bimetallic loading of platinum and copper or palladium and cobalt. In this aspect of the invention, the loading of platinum or palladium is about 0.5 weight percent to about 1 weight percent and the loading of copper or cobalt is about 0.1 weight percent to about 5 weight percent. Specifically, platinum/copper or palladium/cobalt loading levels of 1/1, 1/5, 0.5/0.5, and 0.5/2.5 weight percent on high purity low surface area silica can be used. Other preferred supports in this aspect of the invention include H-ZSM-5, graphitized carbon, zirconia, titania, iron oxide, silica-alumina and calcium silicate.

In another embodiment of this invention, there is further provided a hydrogenation catalyst wherein the bimetallic catalyst is copper and chromium supported on silica, zirconia, graphitized carbon, H-ZSM-5, titania-silica and zirconia-silica. In this aspect of the invention, the loading level of copper and chromium is about 3 weight percent to about 10 weight percent each. Specifically, copper/chromium loading levels of 5 weight percent each on any of the aforementioned catalyst support is preferred.

In general, by the practice of this invention, acetic acid can selectively be converted to ethyl acetate at very high rates. The selectivity to ethyl acetate in general is very high and may be at least 60 percent. Under preferred reaction conditions, acetic acid is selectively converted to ethyl acetate at a selectivity of greater than 85 or 87.5 percent or more preferably at a selectivity of 90 percent or more. Most preferably ethyl acetate selectivity is at least 95 percent.

The conversion of acetic acid using the catalysts of this invention is at least 20% and can be up to 70% with selectivity to ethyl acetate at least 60%, preferably 80% and most preferably 95%.

Generally, the active catalysts of the invention are the single metal or the bimetallic catalysts as described herein. More specifically, a bimetallic catalyst containing platinum and copper supported on silica with a platinum loading of 1 weight percent and copper loading of 5 weight percent is preferred. In accordance with the practice of this invention, acetic acid can be converted using this catalyst at conversions of around 70% with ethyl acetate selectivity of at least 80%, more preferably selectivity to ethyl acetate of at least 90% can be achieved.

Similar conversions and selectivities are achieved using zirconia, graphite or titania as a support and with loadings of platinum and copper of one weight percent and five weight percent respectively. Other promoter metals can also be used in conjunction with palladium or platinum as noted above.

In another aspect of this invention it is also possible to obtain high levels of conversions in the order of at least 25% and high selectivity to ethyl acetate of at least about 90% using palladium loading of one weight percent and cobalt loading of five weight percent on silica or H-ZSM-5 as catalyst supports. In this aspect of the invention, other preferred catalyst supports include graphitized carbon, titania, zirconia, iron oxide, silica-alumina and calcium silicate.

In another aspect of the process of this invention, the hydrogenation is carried out at a pressure just sufficient to overcome the pressure drop across the catalytic bed.

The reaction may be carried out in the vapor or liquid state under a wide variety of conditions. Preferably, the reaction is carried out in the vapor phase. Reaction temperatures may be employed, for example in the range of about 200° C. to about 300° C., preferably about 225° C. to about 275° C. The pressure is generally uncritical to the reaction and subatmospheric, atmospheric or superatmospheric pressures may be employed. In most cases, however, the pressure of the reaction will be in the range of about 5 to 30 atmospheres absolute, most preferably the pressure of reaction zone is in the range of about 8 to 20 atmospheres absolute.

Although the reaction consumes a mole of hydrogen per mole of acetic acid to produce a mole of ethyl acetate, the actual molar ratio of acetic acid to hydrogen in the feed stream may be varied between wide limits, e.g. from about 100:1 to 1:100. It is preferred however that such ratio be in the range of about 1:20 to 1:2. More preferably the molar ratio of acetic acid to hydrogen is about 1:5.

The raw materials used in connection with the process of this invention may be derived from any suitable source including natural gas, petroleum, coal, biomass and so forth. It is well known to produce acetic acid through methanol carbonylation, acetaldehyde oxidation, ethylene oxidation, oxidative fermentation, and anaerobic fermentation and so forth. As petroleum and natural gas have become more expensive, methods for producing acetic acid and intermediates such as methanol and carbon monoxide from alternate carbon sources have drawn more interest. Of particular interest is the production of acetic acid from synthesis gas (syngas) that may be derived from any suitable carbon source. U.S. Pat. No. 6,232,352 to Vidalin, the disclosure of which is incorporated herein by reference, for example teaches a method of retrofitting a methanol plant for the manufacture of acetic acid. By retrofitting a methanol plant the large capital costs associated with CO generation for a new acetic acid plant are significantly reduced or largely eliminated. All or part of the syngas is diverted from the methanol synthesis loop and supplied to a separator unit to recover CO and hydrogen, which are then used to produce acetic acid. In addition to acetic acid, the process can also be used to make hydrogen which is utilized in connection with this invention.

U.S. Pat. No. RE 35,377 Steinberg et al., also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form synthesis gas. The syngas is converted to methanol which may be carbonylated to acetic acid. The method likewise produces hydrogen which may be used in connection with this invention as noted above. See also, U.S. Pat. No. 5,821,111 Grady et al., which discloses a process for converting waste biomass through gasification into synthesis gas as well as U.S. Pat. No. 6,685,754 Kindig et al., the disclosures of which are incorporated herein by reference.

The acetic acid may be vaporized at the reaction temperature, and then it can be fed along with hydrogen in undiluted state or diluted with a relatively inert carrier gas, such as nitrogen, argon, helium, carbon dioxide and the like.

Alternatively, acetic acid in vapor form may be taken directly as crude product from the flash vessel of a methanol carbonylation unit of the class described in U.S. Pat. No. 6,657,078 of Scates et al., the disclosure of which is incorporated herein by reference. The crude vapor product may be fed directly to the reaction zones of the present invention without the need for condensing the acetic acid and light ends or removing water, saving overall processing costs.

Contact or residence time can also vary widely, depending upon such variables as amount of acetic acid, catalyst, reactor, temperature and pressure. Typical contact times range from a fraction of a second to more than several hours when a catalyst system other than a fixed bed is used, with preferred contact times, at least for vapor phase reactions, between about 0.5 and 100 seconds.

Typically, the catalyst is employed in a fixed bed reactor e.g. in the shape of an elongated pipe or tube where the reactants, typically in the vapor form, are passed over or through the catalyst. Other reactors, such as fluid or ebullient bed reactors, can be employed, if desired. In some instances, it is advantageous to use the hydrogenation catalysts in conjunction with an inert material to regulate the pressure drop, flow, heat balance or other process parameters in the catalyst bed including the contact time of the reactant compounds with the catalyst particles.

In one of the preferred embodiments there is also provided a process for selective and direct formation of ethyl acetate from acetic acid comprising: contacting a feed stream containing acetic acid and hydrogen at an elevated temperature with a suitable hydrogenating catalyst containing about 0.5 weight percent to about 1 weight percent of platinum or palladium and about 2.5 weight percent to about 5 weight percent of copper or cobalt on a suitable catalyst support. Preferred catalyst support in this embodiment of the invention is either silica or H-ZSM-5.

In this embodiment of the process of this invention, the preferred hydrogenation catalyst contains about one (1) weight percent platinum and about five (5) weight percent copper or about one (1) weight percent palladium and about five (5) weight percent cobalt. In this embodiment of the process of this invention it is preferred that the hydrogenation catalysts are layered in a fixed bed and the reaction is carried out in the vapor phase using a feed stream of acetic acid and hydrogen in the molar range of about 1:20 to 1:5 and at a temperature in the range of about 225° C. to 275° C. and at a pressure of reaction zones in the range of about 8 to 20 atmospheres absolute, and the contact time of reactants is in the range of about 0.5 and 100 seconds.

The following examples describe the procedures used for the preparation of various catalysts employed in the examples which follow.

Example A

Preparation of 1 Weight Percent Platinum and 5 Weight Percent Copper on High Purity Low Surface Area Silica Powdered and meshed high purity low surface area silica (94 g) of uniform particle size distribution of about 0.2 mm was dried at 120° C. in an oven under nitrogen atmosphere overnight and then cooled to room temperature. To this was added a solution of platinum nitrate (Chempur) (1.64 g) in distilled water (16 ml). The resulting slurry was dried in an oven gradually heated to 110° C. (>2 hours, 10° C./min). The impregnated catalyst mixture was then calcined at 500° C. (6 hours, 1° C./min). To this calcined and cooled material was added a solution of copper nitrate trihydrate (Alfa Aesar) (19 g) in distilled water (19 ml). The resulting slurry was dried in an oven gradually heated to 110° C. (>2 hours, 10° C./min). The impregnated catalyst mixture was then calcined at 500° C. (6 hours, 1° C./min).

Example B

Preparation of 1 Weight Percent Palladium and 5 Weight Percent Cobalt on High Purity Low Surface Area Silica Powdered and meshed high purity low surface area silica (94 g) of uniform particle size distribution of about 0.2 mm was dried at 120° C. in an oven under nitrogen atmosphere overnight and then cooled to room temperature. To this was added a solution of palladium nitrate (Heraeus) (2.17 g) in distilled water (22 ml). The resulting slurry was dried in an oven gradually heated to 110° C. (>2 hours, 10° C./min). The impregnated catalyst mixture was then calcined at 500° C. (6 hours, 1° C./min). To this calcined and cooled material was added a solution of cobalt nitrate hexahydrate (24.7 g) in distilled water (25 ml). The resulting slurry was dried in an oven gradually heated to 110° C. (>2 hours, 10° C./min). The impregnated catalyst mixture was then calcined at 500° C. (6 hours, 1° C./min).

Example C

Preparation of 1 Weight Percent Palladium and 5 Weight Percent Cobalt on H-ZSM-5

The procedures of Example B were substantially repeated except for utilizing H-ZSM-5 as the catalyst support.

Example D

Preparation of 5 Weight Percent Copper and 5 Weight Percent Chromium on High Purity Low Surface Area Silica Powdered and meshed high purity low surface area silica (90 g) of uniform particle size distribution of about 0.2 mm was dried at 120° C. in an oven under nitrogen atmosphere overnight and then cooled to room temperature. To this was added a solution of copper nitrate trihydrate (Alfa Aesar) (19 g) in distilled water (19 ml). The resulting slurry was dried in an oven gradually heated to 110° C. (>2 hours, 10° C./min). The impregnated catalyst mixture was then calcined at 500° C. (6 hours, 1° C./min). To this calcined and cooled material was added a solution of chromium nitrate nonahydrate (Alfa Aesar) (32.5 g) in distilled water (65 ml). The resulting slurry was dried in an oven gradually heated to 110° C. (>2 hours, 10° C./min). The impregnated catalyst mixture was then calcined at 500° C. (6 hours, 1° C./min).

Example E

Preparation of 5 Weight Percent Molybdenum Carbide ($MoC_2$) on High Purity Low Surface Area Silica Powdered and meshed high purity low surface area silica (95 g) of uniform particle size distribution of about 0.2 mm was dried at 120° C. in an oven under nitrogen atmosphere overnight and then cooled to room temperature. To this was added a solution of ammonium heptamolybdate hexahydrate (Sigma) (9.5 g) in distilled water (63 ml). The resulting slurry was dried in an oven gradually heated to 110° C. (>2 hours, 110° C./min). The impregnated catalyst mixture was then calcined at 500° C. (6 hours, 1° C./min). This results in molybdenum oxide on silica. It was then treated in a flow of methane at 500° C. to afford the titled catalyst.

Example F

Preparation of 1 Weight Percent Platinum and 5 Weight Percent Molybdenum on Titania Powdered and meshed titania (94 g) of uniform particle size distribution of about 0.2 mm was dried at 120° C. in an oven under nitrogen atmosphere overnight and then cooled to room temperature. To this was added a solution of platinum nitrate (Chempur) (1.64 g) in distilled water (16 ml). The resulting slurry was dried in an oven gradually heated to 110° C. (>2 hours, 10° C./min). The impregnated catalyst mixture was then calcined at 500° C. (6 hours, 1° C./min). To this calcined and cooled material was added a solution of ammonium heptamolybdate hexahydrate (Sigma) (9.5 g) in distilled water (63 ml). The resulting slurry was dried in an oven gradually heated to 110° C. (>2 hours, 10° C./min). The impregnated catalyst mixture was then calcined at 500° C. (6 hours, 1° C./min).

Example G

Preparation of 1 Weight Percent Palladium on High Purity Low Surface Area Silica Powdered and meshed high purity low surface area silica (99 g) of uniform particle size distribution of about 0.2 mm was dried at 120° C. in an oven under nitrogen atmosphere overnight and then cooled to room temperature. To this was added a solution of palladium nitrate (Heraeus) (2.17 g) in distilled water (22 ml). The resulting slurry was dried in an oven gradually heated to 110° C. (>2 hours, 10° C./min). The impregnated catalyst mixture was then calcined at 500° C. (6 hours, 1° C./min).

Example H

Preparation of 1 Weight Percent Palladium and 5 Weight Percent Molybdenum on H-ZSM-5

The procedures of Example A were substantially repeated except for utilizing a solution of palladium nitrate (Heraeus) (2.17 g) in distilled water (22 ml), a solution of ammonium heptamolybdate hexahydrate (Sigma) (9.5 g) in distilled water (65 ml) and 94 grams of H-ZSM-5. The catalyst was sequentially impregnated first with molybdenum and then with palladium.

Example I

Preparation of 1 Weight Percent Nickel and 5 Weight Percent Molybdenum on Carbon The procedures of Example A were substantially repeated except for utilizing a solution of nickel nitrate hexahydrate (Alfa Aesar) (4.96 g) in distilled water (5 ml), a solution of ammonium heptamolybdate hexahydrate (Sigma) (9.5 g) in distilled water (65 ml) and 94 grams of carbon. The catalyst was sequentially impregnated first with molybdenum and then with nickel.

Example J

Preparation of 1 Weight Percent Platinum on Titania

The procedures of Example A were substantially repeated except for utilizing a solution of platinum nitrate (Chempur) (1.64 g) in distilled water (16 ml) and 99 grams of titania.

Example K

Preparation of 1 Weight Percent Palladium and 5 Weight Percent Rhenium on Titania The procedures of Example A were substantially repeated except for utilizing a solution of palladium nitrate (Heraeus) (2.17 g) in distilled water (22 ml), a solution of perrhenic acid (7 g) in distilled water (14 ml) and 94 grams of titania. The catalyst was sequentially impregnated first with rhenium and then with palladium.

Example L

Preparation of 1 Weight Percent Platinum and 5 Weight Percent Molybdenum on Carbon The procedures of Example F were substantially repeated except for utilizing 94 grams of carbon.

Example M

Preparation of 1 Weight Percent Palladium and 5 Weight Percent Zirconium on Silica The procedures of Example A were substantially repeated except for utilizing a solution of palladium nitrate (Heraeus) (2.17 g) in distilled water (22 ml), a solution of zirconium nitrate pentahydrate (23.5 g) in distilled water (100 ml) and 94 grams of silica. The catalyst was sequentially impregnated first with zirconium and then with palladium.

Example N

Preparation of 1 Weight Percent Platinum and 5 Weight Percent Copper on Titania The procedures of Example A were substantially repeated except for utilizing 94 grams of titania.

Example O

Preparation of 1 Weight Percent Nickel and 5 Weight Percent Rhenium on Titania The procedures of Example A were substantially repeated except for utilizing a solution of nickel nitrate hexahydrate (Alfa Aesar) (4.96 g) in distilled water (5 ml), a solution of perrhenic acid (7 g) in distilled water (14 ml) and 94 grams of titania. The catalyst was sequentially impregnated first with rhenium and then with nickel.

Example P

Preparation of 1 Weight Percent Platinum and 5 Weight Percent Molybdenum on Silica The procedures of Example F were substantially repeated except for utilizing 94 grams of silica.

Example Q

Preparation of 1 Weight Percent Palladium and 5 Weight Percent Molybdenum on Silica The procedures of Example H were substantially repeated except for utilizing 94 grams of silica.

Example R

Preparation of 5 Weight Percent Copper and 5 Weight Percent Zirconium on Silica The procedures of Example A were substantially repeated except for utilizing a solution of copper nitrate trihydrate (Alfa Aesar) (19 g) in distilled water (19 ml), a solution of zirconium nitrate pentahydrate (23.5 g) in distilled water (100 ml) and 94 grams of silica. The catalyst was sequentially impregnated first with copper and then with zirconium.

Gas Chromatographic (GC) Analysis of the Products

The analysis of the products was carried out by online GC. A three channel compact GC equipped with one flame ionization detector (FID) and 2 thermal conducting detectors (TCDs) was used to analyze the reactants and products. The front channel was equipped with an FID and a CP-Sil 5 (20 m)+WaxFFap (5 m) column and was used to quantify:

Acetaldehyde
Ethanol
Acetone
Methyl acetate
Vinyl acetate
Ethyl acetate
Acetic acid
Ethylene glycol diacetate
Ethylene glycol
Ethylidene diacetate
Paraldehyde The middle channel was equipped with a TCD and Porabond Q column and was used to quantify:

$CO_2$
Ethylene
Ethane

The back channel was equipped with a TCD and Molsieve 5A column and was used to quantify:

Helium
Hydrogen
Nitrogen
Methane
Carbon monoxide

Prior to reactions, the retention time of the different components was determined by spiking with individual compounds and the GCs were calibrated either with a calibration gas of known composition or with liquid solutions of known compositions. This allowed the determination of the response factors for the various components.

Example 1

The catalyst utilized was 1 weight percent platinum and 5 weight percent copper on silica prepared in accordance with the procedure of Example A.

In a tubular reactor made of stainless steel, having an internal diameter of 30 mm and capable of being raised to a controlled temperature, there are arranged 50 ml of 1 weight percent platinum and 5 weight percent copper on silica. The length of the catalyst bed after charging was approximately about 70 mm. Prior to the reaction the catalyst was reduced in situ by heating at a rate of 2° C./min to a final temperature of 400° C. Then, 5 mol % hydrogen in nitrogen was introduced to the catalyst chamber at a gas hourly space velocity (GHSV) of 7500 $h^{-1}$. After reduction, the catalyst was cooled to reaction temperature of 275° C. by continuing the gas flow of 5 mol % hydrogen in nitrogen. Once the reaction temperature was stabilized at 275° C. the hydrogenation of acetic acid was begun as follows.

A feed liquid was comprised essentially of acetic acid. The reaction feed liquid was evaporated and charged to the reactor along with hydrogen and helium as a carrier gas with an average combined gas hourly space velocity (GHSV) of about 1250 hr$^{-1}$ at a temperature of about 275° C. and pressure of 15 bar. The resulting feed stream contained a mole percent of acetic acid from about 4.4% to about 13.8% and the mole percent of hydrogen from about 14% to about 77%. A portion of the vapor effluent was passed through a gas chromatograph for analysis of the contents of the effluents. The selectivity to ethyl acetate was 88.5% at a conversion of acetic acid of 37%.

Example 2

The catalyst utilized was 1 weight percent palladium and 5 weight percent cobalt on silica prepared in accordance with the procedure of Example B.

The procedure as set forth in Example 1 was substantially repeated with an average combined gas hourly space velocity (GHSV) of 2,500 hr$^{-1}$ of the feed stream of the vaporized acetic acid and hydrogen (H$_2$ to acetic acid mole ratio of 5) at a temperature of 250° C. and pressure of 8 bar. A portion of the vapor effluent is passed through a gas chromatograph for analysis of the contents of the effluents. The acetic acid conversion was 26% and ethyl acetate selectivity was 91%.

Example 3

The catalyst utilized was 1 weight percent palladium and 5 weight percent cobalt on H-ZSM-5 prepared in accordance with the procedure of Example C.

The procedure as set forth in Example 1 was substantially repeated with an average combined gas hourly space velocity (GHSV) of 2,500 hr$^{-1}$ of the feed stream of the vaporized acetic acid and hydrogen (H$_2$ to acetic acid mole ratio of 5) at a temperature of 250° C. and pressure of 15 bar. A portion of the vapor effluent is passed through a gas chromatograph for analysis of the contents of the effluents. The acetic acid conversion was 18% and ethyl acetate selectivity was 93%.

Example 4

The catalyst utilized was 1 weight percent palladium and 5 weight percent cobalt on H-ZSM-5 prepared in accordance with the procedure of Example C.

The procedure as set forth in Example 1 was substantially repeated with an average combined gas hourly space velocity (GHSV) of 10,000 hr$^{-1}$ of the feed stream of the vaporized acetic acid and hydrogen (H$_2$ to acetic acid mole ratio of 5) at a temperature of 250° C. and pressure of 1 bar. A portion of the vapor effluent is passed through a gas chromatograph for analysis of the contents of the effluents. The acetic acid conversion was 6% and ethyl acetate selectivity was 96%. The other products formed were ethane (1.8%) and ethanol (0.3%).

Example 5

The catalyst utilized was 1 weight percent palladium and 5 weight percent molybdenum on H-ZSM-5 prepared in accordance with the procedure of Example H.

The procedure as set forth in Example 1 was substantially repeated with an average combined gas hourly space velocity (GHSV) of 2,500 hr$^{-1}$ of the feed stream of the vaporized acetic acid and hydrogen (H$_2$ to acetic acid mole ratio of 5) at a temperature of 250° C. and pressure of 15 bar. A portion of the vapor effluent is passed through a gas chromatograph for analysis of the contents of the effluents. The acetic acid conversion was 18% and ethyl acetate selectivity was 93%. The other products formed were ethane (4.3%) and ethanol (0.2%).

Example 6

The catalyst utilized was 1 weight percent nickel and 5 weight percent molybdenum on carbon prepared in accordance with the procedure of Example I.

The procedure as set forth in Example 1 is substantially repeated with an average combined gas hourly space velocity (GHSV) of 2,500 hr$^{-1}$ of the feed stream of the vaporized acetic acid and hydrogen (H$_2$ to acetic acid mole ratio of 5) at a temperature of 250° C. and pressure of 15 bar. A portion of the vapor effluent is passed through a gas chromatograph for analysis of the contents of the effluents. The acetic acid conversion was 6% and ethyl acetate selectivity was 88%. The other products formed were ethane (3.3%) and ethanol (4.9%).

Example 7

The catalyst utilized was 1 weight percent platinum on titania prepared in accordance with the procedure of Example J.

The procedure as set forth in Example 1 is substantially repeated with an average combined gas hourly space velocity (GHSV) of 2,500 hr$^{-1}$ of the feed stream of the vaporized acetic acid and hydrogen (H$_2$ to acetic acid mole ratio of 5) at a temperature of 250° C. and pressure of 15 bar. A portion of the vapor effluent is passed through a gas chromatograph for analysis of the contents of the effluents. The acetic acid conversion was 41% and ethyl acetate selectivity was 88%. The other products formed were ethane (4.8%) and methane (1.7%).

Example 8

The catalyst utilized was the same catalyst used in Example 7 which was reused in this Example 8.

The procedure as set forth in Example 1 is substantially repeated with an average combined gas hourly space velocity (GHSV) of 2,500 hr$^{-1}$ of the feed stream of the vaporized acetic acid and hydrogen (H$_2$ to acetic acid mole ratio of 5) at a temperature of 250° C. and pressure of 15 bar. A portion of the vapor effluent is passed through a gas chromatograph for analysis of the contents of the effluents. The acetic acid conversion was 41% and ethyl acetate selectivity was 87%. The other products formed were ethane (5%) and methane (1.7%).

Example 9

The catalyst utilized was 1 weight percent palladium and 5 weight percent rhenium on titania prepared in accordance with the procedure of Example K.

The procedure as set forth in Example 1 is substantially repeated with an average combined gas hourly space velocity (GHSV) of 2,500 hr$^{-1}$ of the feed stream of the vaporized acetic acid and hydrogen (H$_2$ to acetic acid mole ratio of 5) at a temperature of 250° C. and pressure of 15 bar. A portion of the vapor effluent is passed through a gas chromatograph for analysis of the contents of the effluents. The acetic acid conversion was 61% and ethyl acetate selectivity was 87%. The other products formed were ethanol (11%) and acetaldehyde (1.3%).

Example 10A

The catalyst utilized was 1 weight percent platinum and 5 weight percent molybdenum on carbon prepared in accordance with the procedure of Example L.

The procedure as set forth in Example 1 is substantially repeated with an average combined gas hourly space velocity (GHSV) of 2,500 hr$^{-1}$ of the feed stream of the vaporized acetic acid and hydrogen ($H_2$ to acetic acid mole ratio of 5) at a temperature of 250° C. and pressure of 15 bar. A portion of the vapor effluent is passed through a gas chromatograph for analysis of the contents of the effluents. The acetic acid conversion was 15% and ethyl acetate selectivity was 85%. The other products formed were ethane (7.1%) and ethanol (5.2%).

Example 10B

The catalyst utilized was 1 weight percent palladium and 5 weight percent zirconium on silica prepared in accordance with the procedure of Example M.

The procedure as set forth in Example 1 is substantially repeated with an average combined gas hourly space velocity (GHSV) of 2,500 hr$^{-1}$ of the feed stream of the vaporized acetic acid and hydrogen ($H_2$ to acetic acid mole ratio of 5) at a temperature of 250° C. and pressure of 15 bar. A portion of the vapor effluent is passed through a gas chromatograph for analysis of the contents of the effluents. The acetic acid conversion was 8.3% and ethyl acetate selectivity was 84%. The other products formed were methane (7.9%) and ethane (1%).

Example 10C

The catalyst utilized was 1 weight percent platinum and 5 weight percent copper on titania prepared in accordance with the procedure of Example N.

The procedure as set forth in Example 1 is substantially repeated with an average combined gas hourly space velocity (GHSV) of 2,500 hr$^{-1}$ of the feed stream of the vaporized acetic acid and hydrogen ($H_2$ to acetic acid mole ratio of 5) at a temperature of 250° C. and pressure of 15 bar. A portion of the vapor effluent is passed through a gas chromatograph for analysis of the contents of the effluents. The acetic acid conversion was 10% and ethyl acetate selectivity was 84%. The other products formed were acetone (8.4%) and acetaldehyde (7.1%).

Example 10D

The catalyst utilized was 1 weight percent nickel and 5 weight percent rhenium on titania prepared in accordance with the procedure of Example O.

The procedure as set forth in Example 1 is substantially repeated with an average combined gas hourly space velocity (GHSV) of 2,500 hr$^{-1}$ of the feed stream of the vaporized acetic acid and hydrogen ($H_2$ to acetic acid mole ratio of 5) at a temperature of 250° C. and pressure of 15 bar. A portion of the vapor effluent is passed through a gas chromatograph for analysis of the contents of the effluents. The acetic acid conversion was 16.2% and ethyl acetate selectivity was 83%. The other products formed were ethanol (10.4%) and ethane (2%).

Example 10E

The catalyst utilized was 1 weight percent platinum and 5 weight percent molybdenum on silica prepared in accordance with the procedure of Example P.

The procedure as set forth in Example 1 is substantially repeated with an average combined gas hourly space velocity (GHSV) of 2,500 hr$^{-1}$ of the feed stream of the vaporized acetic acid and hydrogen ($H_2$ to acetic acid mole ratio of 5) at a temperature of 250° C. and pressure of 15 bar. A portion of the vapor effluent is passed through a gas chromatograph for analysis of the contents of the effluents. The acetic acid conversion was 14.3% and ethyl acetate selectivity was 82.4%. The other products formed were ethane (6.6%) and ethanol (5.7%).

Example 10F

The catalyst utilized was 1 weight percent palladium and 5 weight percent molybdenum on silica prepared in accordance with the procedure of Example Q.

The procedure as set forth in Example 1 is substantially repeated with an average combined gas hourly space velocity (GHSV) of 2,500 hr$^{-1}$ of the feed stream of the vaporized acetic acid and hydrogen ($H_2$ to acetic acid mole ratio of 5) at a temperature of 250° C. and pressure of 15 bar. A portion of the vapor effluent is passed through a gas chromatograph for analysis of the contents of the effluents. The acetic acid conversion was 9.8% and ethyl acetate selectivity was 82%. The other products formed were ethanol (8.3%) and ethane (3.5%).

Example 10G

The catalyst utilized was 5 weight percent copper and 5 weight percent zirconium on silica prepared in accordance with the procedure of Example R.

The procedure as set forth in Example 1 is substantially repeated with an average combined gas hourly space velocity (GHSV) of 2,500 hr$^{-1}$ of the feed stream of the vaporized acetic acid and hydrogen ($H_2$ to acetic acid mole ratio of 5) at a temperature of 250° C. and pressure of 15 bar. A portion of the vapor effluent is passed through a gas chromatograph for analysis of the contents of the effluents. The acetic acid conversion was 2.2% and ethyl acetate selectivity was 81.4%. The other products formed were ethane (3.3%) and acetaldehyde (10%).

Example 10H

The catalyst utilized was 5 weight percent copper and 5 weight percent chromium on silica prepared in accordance with the procedure of Example D.

The procedure as set forth in Example 1 is substantially repeated with an average combined gas hourly space velocity (GHSV) of 2,500 hr$^{-1}$ of the feed stream of the vaporized acetic acid and hydrogen at a temperature of 250° C. and pressure of 15 bar. A portion of the vapor effluent is passed through a gas chromatograph for analysis of the contents of the effluents. The acetic acid conversion is 25% and ethyl acetate selectivity is about 75%.

Example 10I

The catalyst utilized was 5 weight percent Molybdenum Carbide ($MoC_2$) on High Purity Low Surface Area Silica prepared in accordance with the procedure of Example E.

The procedure as set forth in Example 1 is substantially repeated with an average combined gas hourly space velocity (GHSV) of 2,500 hr$^{-1}$ of the feed stream of the vaporized acetic acid and hydrogen at a temperature of 250° C. and pressure of 15 bar. A portion of the vapor effluent is passed through a gas chromatograph for analysis of the contents of the effluents. The acetic acid conversion is 25% and ethyl acetate selectivity is 75%.

Example 10J

The catalyst utilized was 1 weight percent platinum and 5 weight percent molybdenum on titania prepared in accordance with the procedure of Example F.

The procedure as set forth in Example 1 is substantially repeated with an average combined gas hourly space velocity (GHSV) of 2,500 hr$^{-1}$ of the feed stream of the vaporized acetic acid and hydrogen at a temperature of 250° C. and pressure of 15 bar. A portion of the vapor effluent is passed through a gas chromatograph for analysis of the contents of the effluents. The acetic acid conversion is about 50% and ethyl acetate selectivity is 85%.

Example 10K

The catalyst utilized was 1 weight percent palladium on silica prepared in accordance with the procedure of Example G.

The procedure as set forth in Example 1 is substantially repeated with an average combined gas hourly space velocity (GHSV) of 2,500 hr$^{-1}$ of the feed stream of the vaporized acetic acid and hydrogen at a temperature of 250° C. and pressure of 15 bar. A portion of the vapor effluent is passed through a gas chromatograph for analysis of the contents of the effluents. The acetic acid conversion is about 65% and ethyl acetate selectivity is 85%.

While the invention has been illustrated in connection with particular examples, modifications to these examples within the spirit and scope of the invention will be readily apparent to those of skill in the art. In view of the foregoing discussion, relevant knowledge in the art and references discussed above in connection with the Background and Detailed Description, the disclosures of which are all incorporated herein by reference, further description is deemed unnecessary.

What is claimed is:

1. A process for selective and direct formation of ethyl acetate from acetic acid comprising: contacting a feed stream containing acetic acid and hydrogen at an elevated temperature at an operating pressure of about 5 to about 30 atmospheres absolute with a hydrogenating catalyst consisting essentially of at least one metal selected from the group consisting of nickel, platinum and palladium and at least one metal selected from copper and cobalt supported on a catalyst support selected from the group consisting of H-ZSM-5, silica, alumina, silica-alumina, calcium silicate, carbon, and mixtures.

2. The process according to claim 1, wherein the catalyst support is silica.

3. The process according to claim 1, wherein the catalyst support is H-ZSM-5.

4. The process according to claim 1, wherein the catalyst support is carbon.

5. The process according to claim 4, wherein the catalyst support is graphite.

6. The process according to claim 5, wherein the catalyst support is high surface area graphitized carbon having a BET surface area of at least 100 m$^2$/g.

7. The process according to claim 1, wherein the hydrogenating catalyst consists essentially of platinum and copper at a Pt/Cu weight ratio in the range of about 0.1 to 1.

8. The process according to claim 7, wherein the loading of platinum is about 0.5 weight percent and the loading of copper is about 2.5 weight percent and the catalyst support is silica, graphite, or silica-alumina.

9. The process according to claim 7, wherein the loading of platinum is about 1 weight percent and the loading of copper is about 5 weight percent and the catalyst support is silica, graphite, or silica-alumina.

10. The process according to claim 1, wherein the hydrogenating catalyst consists essentially of palladium and cobalt at a Pd/Co weight ratio in the range of about 0.1 to 1.

11. The process according to claim 10, wherein the loading of palladium is about 1 weight percent and the loading of cobalt is about 5 weight percent and the catalyst support is H-ZSM-5, silica, graphite, or silica-alumina.

12. The process according to claim 1, wherein the selectivity to ethyl acetate based on acetic acid consumed is at least 60 percent.

13. The process according to claim 1, wherein the selectivity to ethyl acetate based on acetic acid consumed is greater than 85 percent.

14. The process according to claim 1, wherein the selectivity to ethyl acetate based on acetic acid consumed is 87.5 percent or greater.

15. The process according to claim 1, wherein the selectivity to ethyl acetate based on acetic acid consumed is 90 percent or greater.

16. The process according to claim 1, wherein the hydrogenation to ethyl acetate is carried out in the vapor phase and at a temperature in the range of about 200° C. to 300° C.

17. The process according to claim 16, wherein the hydrogenation to ethyl acetate is carried out in the vapor phase and at a temperature in the range of about 225° C. to 275° C.

18. The process according to claim 16, wherein said feed stream contains an inert carrier gas.

19. The process according to claim 16, wherein the reactants consist of acetic acid and hydrogen with a molar ratio in the range of about 100:1 to 1:100, the temperature of the reaction zone is in the range of about 200° C. to 300° C., and the pressure of the reaction zone is in the range of about 5 to 25 atmospheres absolute.

20. The process according to claim 16, wherein the reactants consist of acetic acid and hydrogen with a molar ratio in the range of about 1:20 to 1:2, the temperature of the reaction zone is in the range of about 225° C. to 275° C., and the pressure of the reaction zone is in the range of about 8 to 20 atmospheres absolute.

21. A process for selective and direct formation of ethyl acetate from acetic acid comprising: contacting a feed stream containing acetic acid and hydrogen at an elevated temperature at an operating pressure of from 5 to 30 atmospheres absolute with a hydrogenating catalyst consisting essentially of about 0.5 weight percent to about 1 weight percent of platinum or palladium and 2.5 weight percent to about 5 weight percent of copper or cobalt on a catalyst support selected from the group consisting of H-ZSM-5, silica, alumina, silica-alumina, calcium silicate, carbon, and mixtures thereof.

22. The process according to claim 21, wherein the catalyst support contains platinum at a loading level of about one (1) weight percent and copper at a loading level of about five (5) weight percent and the catalyst support is silica.

23. The process according to claim 21, wherein the catalyst support contains palladium at a loading level of about one (1)

weight percent and cobalt at a loading level of about five (5) weight percent and the catalyst support is silica or H-ZSM-5.

24. The process according to claim 21, wherein the reactants consist of acetic acid and hydrogen with a molar ratio in the range of about 1:20 to 1:5, the temperature of the reaction zone is in the range of about 225° C. to 275° C., and the pressure of the reaction zone is are in the range of about 8 to 20 atmospheres absolute.

25. The process according to claim 1, wherein the contact time between the feed stream and said catalyst is less than 100 seconds.

26. The process according to claim 1, wherein the gas hourly space velocity of the feed stream in contact with said catalyst is greater than 2500 $hr^{-1}$.

27. The process according to claim 1, wherein the selectivity to ethyl acetate is at least 60%.

28. The process according to claim 1, wherein the selectivity to ethyl acetate is at least 85%.

29. The process according to claim 1, wherein the selectivity to ethyl acetate is at least 87.5%.

30. The process according to claim 1, wherein the selectivity to ethyl acetate is at least 90%.

31. The process according to claim 1, wherein the selectivity to ethyl acetate is at least 95%.

32. The process according to claim 1, wherein the conversion of ethyl acetate is at least 20% and the selectivity to ethyl acetate is at least 95%.

33. The process according to claim 1, wherein the conversion of ethyl acetate is at least 20% and the selectivity to ethyl acetate is at least 80%.

34. The process according to claim 1, wherein the conversion of ethyl acetate is at least 20% and the selectivity to ethyl acetate is at least 60%.

35. The process according to claim 1, wherein the pressure is less than 25 atmospheres absolute.

36. A process for selective and direct formation of ethyl acetate from acetic acid comprising: contacting a feed stream containing acetic acid and hydrogen at an elevated temperature at an operating pressure of from 5 to 30 atmospheres absolute with a hydrogenating catalyst consisting essentially of platinum and tin on a support selected from the group consisting of H-ZSM-5, silica, alumina, silica-alumina, calcium silicate, carbon, and mixtures thereof.

37. A process for selective and direct formation of ethyl acetate from acetic acid comprising: contacting a feed stream containing acetic acid and hydrogen at an elevated temperature at an operating pressure of from 5 to 30 atmospheres absolute with a hydrogenating catalyst containing platinum and tin on a titania-silica support.

38. The process according to claim 37, wherein the contact time between the feed stream and said catalyst is less than 100 seconds.

39. The process according to claim 37, wherein the gas hourly space velocity of the feed stream in contact with said catalyst is greater than 2500 $hr^{-1}$.

40. The process according to claim 37, wherein the selectivity to ethyl acetate is at least 60%.

41. The process according to claim 37, wherein the selectivity to ethyl acetate is at least 85%.

42. The process according to claim 37, wherein the selectivity to ethyl acetate is at least 87.5%.

43. The process according to claim 37, wherein the selectivity to ethyl acetate is at least 90%.

44. The process according to claim 37, wherein the selectivity to ethyl acetate is at least 95%.

45. The process according to claim 37, wherein the conversion of ethyl acetate is at least 20% and the selectivity to ethyl acetate is at least 60%.

46. The process according to claim 37, wherein the conversion of ethyl acetate is at least 20% and the selectivity to ethyl acetate is at least 80%.

47. The process according to claim 37, wherein the conversion of ethyl acetate is at least 20% and the selectivity to ethyl acetate is at least 95%.

48. The process according to claim 37, wherein the pressure is less than 25 atmospheres absolute.

49. The process according to claim 37, wherein the reactants consist of acetic acid and hydrogen with a molar ratio in the range of about 100:1 to 1:100, the temperature of the reaction zone is in the range of about 200° C. to 300° C., and the pressure of the reaction zone is in the range of about 5 to 25 atmospheres absolute.

50. The process according to claim 37, wherein the reactants consist of acetic acid and hydrogen with a molar ratio in the range of about 1:20 to 1:2, the temperature of the reaction zone is in the range of about 225° C. to 275° C., and the pressure of the reaction zone is in the range of about 8 to 20 atmospheres absolute.

51. A process for selective and direct formation of ethyl acetate from acetic acid comprising: contacting a feed stream containing acetic acid and hydrogen at an elevated temperature with a hydrogenating catalyst chosen from a bimetallic combination of nickel/molybdenum (Ni/Mo), palladium/molybdenum (Pd/Mo) or platinum/molybdenum (Pt/Mo) supported on H-ZSM-5.

52. The process according to claim 51, wherein said catalyst is a bimetallic combination of 1 weight percent palladium and 5 weight percent molybdenum (1 wt % Pd/5 wt % Mo) supported on H-ZSM-5.

* * * * *